(12) United States Patent
Goel

(10) Patent No.: US 11,786,274 B2
(45) Date of Patent: Oct. 17, 2023

(54) BONE HOOK APPARATUS

(71) Applicant: NuVasive, Inc., San Diego, CA (US)

(72) Inventor: Prakhar Goel, San Diego, CA (US)

(73) Assignee: NuVasive, Inc., San Diego, CA (US)

(*) Notice: Subject to any disclaimer, the term of this patent is extended or adjusted under 35 U.S.C. 154(b) by 363 days.

(21) Appl. No.: 17/122,873

(22) Filed: Dec. 15, 2020

(65) Prior Publication Data
US 2021/0100591 A1 Apr. 8, 2021

Related U.S. Application Data

(63) Continuation of application No. 16/271,242, filed on Feb. 8, 2019, now Pat. No. 10,893,891, which is a continuation of application No. 15/382,237, filed on Dec. 16, 2016, now Pat. No. 10,206,719.

(51) Int. Cl.
*A61B 17/70* (2006.01)

(52) U.S. Cl.
CPC ........ *A61B 17/7056* (2013.01); *A61B 17/707* (2013.01); *A61B 17/7032* (2013.01)

(58) Field of Classification Search
CPC ............ A61B 17/7056; A61B 17/7032; A61B 17/7002; A61B 17/7011; A61B 17/707
USPC ......... 606/60, 246, 250, 251, 252, 264, 265, 606/276, 277, 279, 308
See application file for complete search history.

(56) References Cited

U.S. PATENT DOCUMENTS

| 5,092,889 | A | 3/1992 | Campbell, Jr. |
| 5,261,908 | A | 11/1993 | Campbell, Jr. |
| 5,334,203 | A | 8/1994 | Wagner |
| 5,632,744 | A | 5/1997 | Campbell, Jr. |
| 5,688,273 | A | 11/1997 | Errico et al. |
| 5,688,274 | A | 11/1997 | Errico et al. |
| 5,800,434 | A | 9/1998 | Campbell, Jr. |
| 6,458,131 | B1 | 10/2002 | Ray |
| 6,589,243 | B1 * | 7/2003 | Viart ............... A61B 17/707 606/276 |
| 6,918,910 | B2 | 7/2005 | Smith et al. |
| 7,029,472 | B1 | 4/2006 | Fortin |
| 8,016,837 | B2 | 9/2011 | Giger et al. |
| 8,236,002 | B2 | 8/2012 | Fortin et al. |
| 8,298,240 | B2 | 10/2012 | Giger et al. |
| 8,337,532 | B1 | 12/2012 | McLean et al. |
| 8,568,457 | B2 | 10/2013 | Hunziker |
| 8,808,328 | B2 | 8/2014 | Hwang |
| 8,894,663 | B2 | 11/2014 | Giger et al. |

(Continued)

FOREIGN PATENT DOCUMENTS

| CA | 2452127 A1 | 6/2006 |
| CA | 2451977 A1 | 7/2008 |

(Continued)

*Primary Examiner* — Eduardo C Robert
*Assistant Examiner* — David C Comstock
(74) *Attorney, Agent, or Firm* — Hoffman Warnick LLC

(57) ABSTRACT

A bone hook apparatus is provided that includes a base, a rod receptacle disposed on a proximal side of the base, a first hook distally extending from the base and oriented in a first direction, and a second hook distally extending from the base and oriented in a second direction opposing the first direction, the first hook and second hook together configured to receive the bone. Kits and spinal constructs employing the bone hook apparatus are also described.

20 Claims, 4 Drawing Sheets

(56) References Cited

U.S. PATENT DOCUMENTS

| | | |
|---|---|---|
| 8,956,392 B2 | 2/2015 | Khatchadourian et al. |
| 8,974,500 B2 | 3/2015 | Khatchadourian et al. |
| 8,979,038 B1 | 3/2015 | Oh |
| 8,992,575 B1 | 3/2015 | Di Lauro et al. |
| 9,204,899 B2 | 12/2015 | Buttermann |
| 9,204,908 B2 | 12/2015 | Buttermann |
| 9,282,997 B2 | 3/2016 | Hunziker |
| 9,314,285 B2 | 4/2016 | Reisberg |
| 10,034,693 B2 | 7/2018 | Stern |
| 10,893,891 B2 * | 1/2021 | Goel ................. A61B 17/7032 |
| 2002/0120272 A1 | 8/2002 | Yuan et al. |
| 2004/0162558 A1 | 8/2004 | Hegde et al. |
| 2005/0234448 A1 | 10/2005 | McCarthy |
| 2006/0229607 A1 | 10/2006 | Brumfield |
| 2008/0051784 A1 | 2/2008 | Gollogly |
| 2010/0004687 A1 | 1/2010 | Falahee |
| 2010/0004697 A1 | 1/2010 | Fortin et al. |
| 2010/0137913 A1 | 6/2010 | Khatchadourian et al. |
| 2010/0280519 A1 | 11/2010 | Soubeiran |
| 2013/0150889 A1 | 6/2013 | Fening et al. |
| 2014/0135853 A1 | 5/2014 | Reisberg |
| 2014/0222074 A1 | 8/2014 | Rathbun et al. |
| 2014/0277147 A1 | 9/2014 | Alexander et al. |
| 2014/0296918 A1 | 10/2014 | Fening et al. |
| 2014/0343612 A1 | 11/2014 | Rezach et al. |
| 2014/0364911 A1 | 12/2014 | Hwang |
| 2015/0134002 A1 | 5/2015 | Khatchadourian et al. |
| 2015/0190174 A1 | 7/2015 | McCarthy et al. |
| 2015/0190178 A1 | 7/2015 | McCarthy et al. |
| 2016/0015430 A1 * | 1/2016 | Buttermann ....... A61B 17/7032 29/434 |
| 2016/0030088 A1 | 2/2016 | Lim et al. |
| 2016/0183981 A1 * | 6/2016 | Schlaepfer ......... A61B 17/7056 606/324 |

FOREIGN PATENT DOCUMENTS

| | | |
|---|---|---|
| CN | 103767778 A | 5/2014 |
| DE | 202012012881 U1 | 5/2014 |
| FR | 2891726 A1 | 2/2008 |
| FR | 2900563 B1 | 8/2008 |
| SU | 1106486 A1 | 8/1984 |
| WO | 1993022989 A1 | 11/1993 |
| WO | 2007051924 A1 | 5/2007 |

* cited by examiner

BONE HOOK APPARATUS

CROSS-REFERENCE TO RELATED APPLICATIONS

This application is a continuation of U.S. patent application Ser. No. 16/271,242 filed Feb. 8, 2019, which is a continuation of U.S. patent application Ser. No. 15/382,237 filed Dec. 16, 2016, which are incorporated by reference herein in their entirety.

FIELD

The present disclosure relates generally to medical devices, more specifically to the field of spinal surgery and spinal fixation devices. Such devices as well as systems and methods for use therewith are described.

BACKGROUND

The spine is critical in human physiology for mobility, support, and balance. The spine protects the nerves of the spinal cord, which convey commands from the brain to the rest of the body, and convey sensory information from the nerves below the neck to the brain. Even minor spinal injuries can be debilitating to the patient, and major spinal injuries can be catastrophic. The loss of the ability to bear weight or permit flexibility can immobilize the patient. Even in less severe cases, small irregularities in the spine can put pressure on the nerves connected to the spinal cord, causing devastating pain and loss of coordination. Surgical procedures on the spine often include the immobilization of two or more vertebrae. Immobilizing the vertebrae may be accomplished in many ways (e.g. fixation plates and pedicle screw systems). One of the most common methods for achieving the desired immobilization is through the application of bone anchors (most often introduced into the pedicles associated with the respective vertebrae to be fixed) that are then connected by rigid rods locked to each pedicle screw. These pedicle screw systems are very effective. However, vertebrae of pediatric patients can be small, making the use of pedicle screws challenging, and the vertebrae of trauma patients, or patients having decreased vertebrae strength, may not have sufficient bone structure with which to use pedicle screw systems. Therefore, a need continues to exist for new bone fixation devices that can be used as alternatives to pedicle screws.

SUMMARY

The needs described above, as well as others, are addressed by embodiments of a bone hook apparatus described in this disclosure (although it is to be understood that not all needs described above will necessarily be addressed by any one embodiment), as the bone hook apparatus of the disclosure is attachable to bone that may be more accessible than a small pedicle and does not require penetrating the bone in order to secure the rigid rod with the bone, and thus, is capable of fastening a bone that may not hold a pedicle screw.

A bone hook apparatus for securing a rod to a bone is provided having a base, a rod receptacle disposed on the base, and at least two hooks distally extending from the base and together configured to receive the bone. The hooks may each have an arm that extends from the base, and a blade that extends from the arm. The first hook may have a first hook length greater than a second hook length of the second hook. The blade of the first hook may extend to a front face plane of the base, and the blade of the second hook may extend to a mid-plane of the base. The first hook may be positioned on the base offset from the second hook. The first hook may have an arm thickness greater than an arm thickness of the second hook. For example, the arm thickness of the first hook may be from 50% to 100% greater than the arm thickness of the second hook.

The bone hook apparatus may be dimensioned to secure the rod to any suitable bone, such as a rib, a transverse process, or a vertebral lamina. The bone hook apparatus may be dimensioned to secure the rod to a bone of a subject of widely varying size, including a pediatric subject or an adult.

An embodiment of the rod receptacle includes two upright arms extending from the base to an upper end and separated by a rod channel. The rod channel may be configured to receive at least a portion of a spinal rod or a similarly dimensioned elongate element. The rod channel may include a seat disposed between the upright arms, the seat shaped complementarily to the rod. At least one of the pair of upright arms may include a tool engagement feature, such as an indentation. The rod receptacle may include a locking cap engagement feature, such as a helically wound flanged guide and advancement feature or a thread, for engaging a locking cap having cooperative features.

The bone hook apparatus may be constructed of a biocompatible material (e.g., titanium, a titanium alloy, steel, a steel alloy, stainless steel, surgical steel, or a combination thereof).

In another aspect, a spinal construct is provided including a rod, a bone hook apparatus, and a bone fastener. The bone hook apparatus includes a first hook, a second hook, and a rod receptacle. The hooks are configured to securely receive at least part of a first bone, and the rod receptacle is configured to receive at least part of the rod. The bone fastener is provided on the rod opposite from the bone hook apparatus, and the bone fastener is configured to secure the rod to a second bone.

In another aspect, a kit is provided, comprising at least one bone hook apparatus including a base, a rod receptacle disposed on a proximal side of the base. The rod receptacle has a locking cap engagement feature. The at least one bone hook apparatus includes at least two hooks distally extending from the base, the at least two hooks oppositely facing and configured to cooperatively receive a bone. The kit includes a rod dimensioned to fit at least partially within the rod receptacle. The kit may further comprise a locking cap configured to engage the locking cap engagement feature to restrict movement of the rod relative to the bone hook apparatus. The kit may be provided with multiple bone hook apparatuses, each having a different diameter.

In another aspect, a method to secure the bone hook apparatus to the bone is provided. The method includes providing the bone hook apparatus and positioning the bone hook apparatus proximate to the bone. The first hook and the second hook are aligned with the bone so the first hook and second hook are substantially parallel with the bone in an initial orientation. The bone hook apparatus is rotated to a final position so as to engage the first hook and the second hook with the bone. The rotation may be a rotation of about 90 degrees.

The above presents a simplified summary in order to provide a basic understanding of some aspects of the claimed subject matter. This summary is not an extensive overview. It is not intended to identify key or critical elements or to delineate the scope of the claimed subject matter. Its sole purpose is to present some concepts in a simplified form as a prelude to the more detailed description that is presented later.

DETAILED DESCRIPTION

Figure 1:
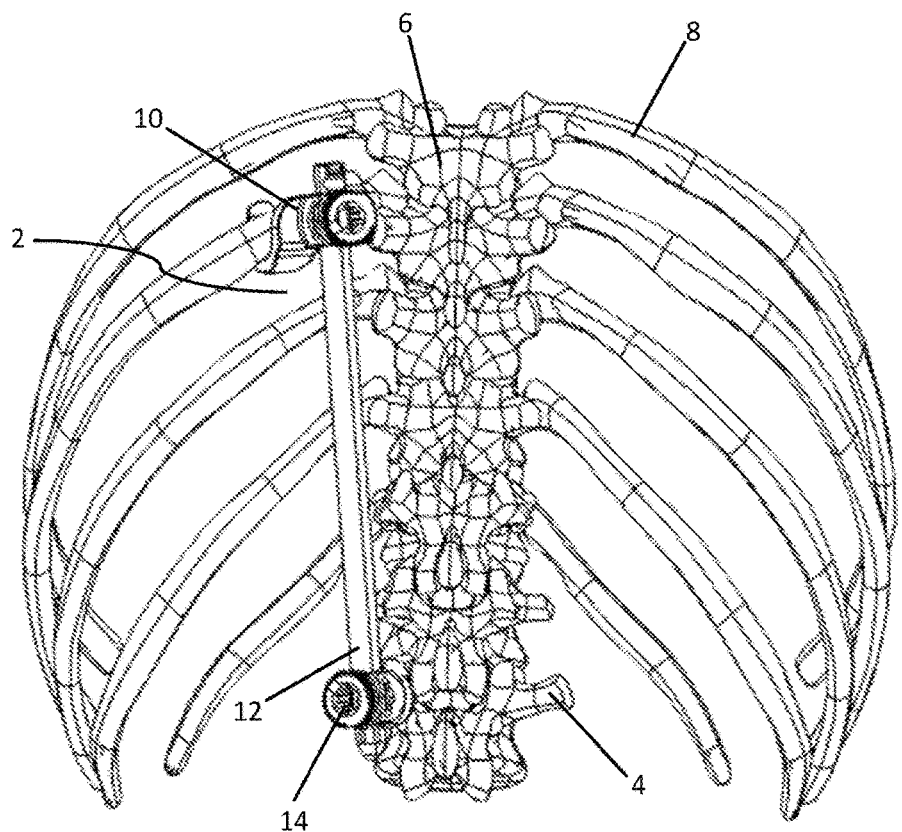
FIG. 1. A front view of an embodiment of a spinal construct having a bone hook apparatus, rod, and a bone fastener in use with a rib cage.

Illustrative embodiments of a bone hook apparatus are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The bone hook apparatus disclosed herein boasts a variety of inventive features and components that warrant patent protection, both individually and in combination.

As used herein, the term "proximal" means the side facing closest to the surgeon when the device is properly implanted, whereas the term "distal" means the side facing away from the surgeon.

A bone hook apparatus 10 is provided for securing a rod 12, such as a spinal fixation rod, to a bone 8, such as a rib bone, a lamina bone, or a transverse process bone. The bone 8 may be that of a pediatric subject, such as a child or an adolescent, or an adult human subject. The pediatric subject may be any age, for example between ages 0-18 years.

In one embodiment, a spinal construct 2 is provided that comprises the bone hook apparatus 10 configured to securely receive each of the rod 12 and the bone 8. A bone fastener 14, such as a pedicle screw, may be provided on the rod 12 opposite from the bone hook apparatus 10. The bone fastener 14 may secure the rod 12 with a second bone 4 (e.g., a pedicle). Advantageously, the construct 2 immobilizes at least one vertebra 6, while not needing an additional point of contact with another vertebra 6, as the additional point of contact is provided by the bone 8.

The bone hook apparatus 10 comprises a base 16 and a rod receptacle 30 for receiving the rod. In the illustrated embodiment of the bone hook apparatus 10, a first hook 18 and a second hook 20 are included. The first hook 18 comprises a first hook arm 22 extending from the base 16 toward a distal end 35. The second hook 20 includes a second hook arm 24 extending from the base 16 toward the distal end 35. The arms 24 and 26 may contact a back side of the bone 8. The first hook arm 22 and the second hook arm 24 have a first blade 26 and a second blade 28, respectively, extending away from the base 16. The first blade 26 and the second blade 28 may each taper to a point or an edge, and contact a back side of the bone 8. The hooks 18 and 20 may each have a substantially C-shaped profile and be positioned distal to the base 16. The openings of the C-shaped profiles in the first hook 18 and the second hook 20 may opposingly face one another. In an embodiment of the bone hook apparatus 10, the bone hook apparatus 10 has exactly two hooks, the first hook 18 and the second hook 20. Advantageously, in embodiments of the bone hook apparatus 10 having the first hook 18 and the second hook 20, function is enhanced, as a surgeon is able to easily position the bone hook apparatus 10 on the bone 8, and rotate the bone hook apparatus 90 degrees and securely capture the bone 8.

The first hook 18 and the second hook 20 may be in various positions and of varying dimensions. For example, in the illustrated embodiment of the bone hook apparatus 10, the first hook 18 and the second hook 20 are positioned offset from one another on the base 16 (shown in FIG. 3). In this embodiment of the bone hook apparatus 10, the first hook 18 originates at or proximate to the junction of a rear face 46 and a first side face 48, and the first hook 18 projects outwardly toward a front face 44. The second hook 20 originates at or proximate to the junction of the front face 44 and a second side face 50, and the second hook 20 projects toward the rear face 46. The front face 44 may be defined as the face toward which the first hook 18 curves while curving away from the rear face 46. The rear face 46 may be defined as the face toward which the second hook 20 curves while curving away from the front face 44.

Figure 10A:
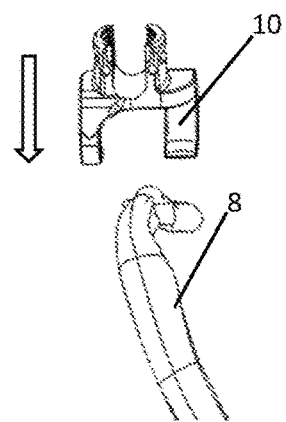
FIG. 10A. A perspective view of the bone hook apparatus shown in FIG. 1 with an associated rib bone.
Figure 10B:
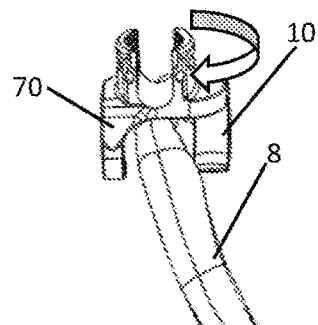
FIG. 10B. A perspective view of the bone hook apparatus shown in FIG. 10A positioned above the associated rib bone.
Figure 10C:
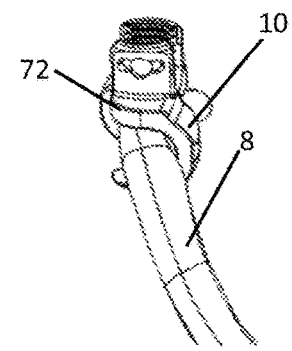
FIG. 10C. A perspective view of the bone hook apparatus shown in FIG. 10B rotated 90 degrees about the bone, trapping the bone between a first hook and a second hook.

As shown in the illustrated embodiment of the bone hook apparatus 10, the rod receptacle 30 comprises at least two upright arms 32 extending from the base 16 to an upper proximal end 34. A rod channel 36 is defined by the upright arms 32 and the base 16. When in use, the rod channel 36 contains at least part of the rod 12; therefore, the rod channel 36 may be dimensioned to accommodate the rod 12 (the rod 12 may be of any suitable dimensions known in the art). The rod channel 36 may take a variety of shapes, and in some embodiments of the bone hook apparatus 10, has a U-shaped seat 38 that is complementary to the rod 12 that may have a cylindrical shape on the proximal side (i.e., the bottom portion of the "U"). Some embodiments of the bone hook apparatus 10 have the rod channel 36 open at the upper proximal end 34 in order to allow the rod 12 to be emplaced from the proximal direction, although other configurations are possible (e.g. the rod receptacle could employ side loading rod channel 36). As shown in FIG. 10F, the bone hook apparatus 10 may have a locking cap engagement feature 42 to receive a locking cap 78. The locking cap 78 may be placed proximal to the rod channel 36, to constrain the rod 12 from proximal displacement. When fully tightened to the locking cap engagement feature 42, the locking cap 78 compresses the rod 12 and constrains the rod 12 from movement relative to the bone hook apparatus 10.

In a certain embodiment of the bone hook apparatus 10, the locking cap engagement feature 42 comprises a helically wound flanged guide and advancement feature or a thread that is dimensioned to cooperate with the locking cap engagement feature 42 (such as complementary helical guides or screw threads (FIG. 10F) of the locking cap 78). The locking cap engagement feature 42 may be configured to exert force with a distal vector on the rod 12, providing a means to reduce the rod 12 and seat the rod 12 in the rod channel 36. As shown in FIGS. 10F and 10G, the locking cap 78 may have a driver engagement feature 88 to allow a driving tool to engage and to drive the cap 78. In the particular illustrated embodiment of the bone hook apparatus 10, the driver engagement feature 88 is a hexalobular internal feature.

The upright arms 32 extend on either side of the rod channel 36. The upright arms 32 may each include an attachment feature 40 for coupling to various tools (e.g., inserters, reducers, and other such tools as are known in the art) useful during implantation of the bone hook apparatus 10 and the construct 2. In the specific embodiment of the bone hook apparatus 10 shown in FIGS. 2-5 and 10C-10G, the attachment feature 40 may comprise a circumferential slot 84 (shown in FIG. 3) on both arms 32 just below the proximal end of each upright arm 32, and an indentation 86 (shown in FIG. 3) that meets the distal side of the circumferential slot 84. Together the circumferential slot 84 and the indentation 86 allow a tool (not shown) to connect to the bone hook apparatus 10 in such a way that the tool will neither translate longitudinally nor rotate circumferentially while attached. Other configurations of course may be used.

In the illustrated embodiment of the bone hook apparatus 10, the first hook 18 has a first arm thickness 58 that is greater than a second arm thickness 60 of the second hook 20. "Thickness" in this context refers to the dimension parallel to an axis of a first passage 52. The first arm thickness 58 may be between 3 mm and 8 mm, or about 5 mm. The second arm thickness 60 may be between 1 mm and 5 mm, or about 3 mm. In an embodiment of the bone hook apparatus 10, the first arm thickness 58 is 5 mm and the second arm thickness is 3 mm. In another embodiment of the bone hook apparatus 10, the first arm thickness 58 is from 50% to 100% greater than the second arm thickness 60. Advantageously, in embodiments of the bone hook apparatus 10 having a greater first arm thickness 58 than a second arm thickness 60, the bone hook apparatus 10 may be orientated to position the thicker first hook 18 in a desired final orientation 72 (shown in FIG. 10C) to provide a wider surface area for load distribution under certain conditions, such as under distraction.

Figure 4:
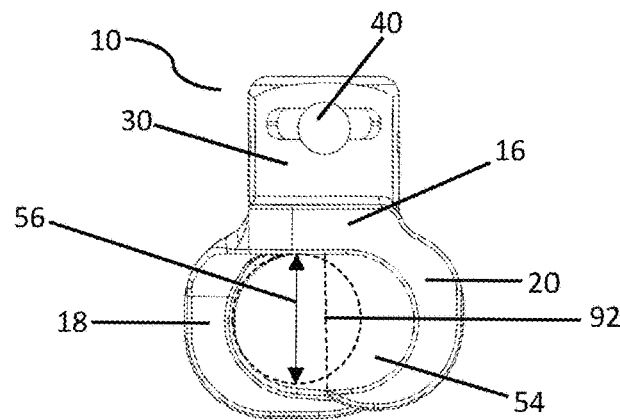
FIG. 4. A top view of the bone hook apparatus shown in FIG. 1.
Figure 5:
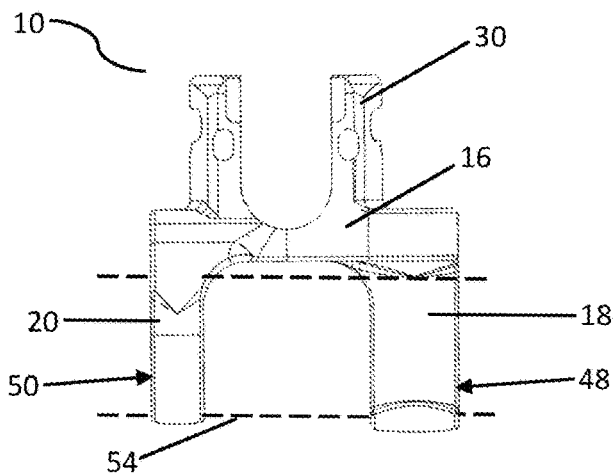
FIG. 5. A side view of the bone hook apparatus shown in FIG. 1.

The bone hook apparatus 10 has a height representing the distance between the base 16 and the hook blades 26 and 28. The hook 18 or 20 may be provided with a height that falls within a range of varying dimensions to accommodate differently sized bones, such as ribs, within the bone hook apparatus 10. The height may be defined according to various measurements. For example, the height may be defined as the distance between the lower surface of the base 16 and the upper surface of the first hook base at the mid-plane 92. Alternatively, as illustrated in FIG. 4, the height may be defined as the diameter of the inner arc of the first hook. That is, a portion of the inner surface of the first hook 18 follows an arc, and the hook diameter is the diameter 56 of the circle that is defined by the arc. According to this example, then, the diameter 56 may be dimensioned to accommodate a rib bone of a child, or a rib bone from an adult subject. In another embodiment of the bone hook apparatus 10, the diameter 56 may be varied to be dimensioned to accommodate a rib bone of an adult female or male. By way of example, the diameter 56 may be from 4 mm to 16 mm, 5 mm to 15 mm, 6 mm to 14 mm, 7 mm to 13 mm, 8 mm to 12 mm, 9 mm to 11 mm, 10 mm, or any combination of these ranges.

A kit is provided including at least one bone hook apparatus 10, the rod 12, and the locking cap 78. The bone hook apparatus 10 in the kit may be any suitable bone hook apparatus 10 described above. The kit may be provided with variously dimensioned hooks 10. In one embodiment, a kit is provided having a plurality of hooks 10, the kit having at least two hooks 10 with diameters 56 independently selected from: 4 mm, 5 mm, 6 mm, 7 mm, 8 mm, 9 mm, 10 mm, 11 mm, 12 mm, 13 mm, 14 mm, 15 mm, and 16 mm. Advantageously, by providing the kit with hooks 10 ranging in diameter 56 from 4 mm to 16 mm in 1 mm increments, a practitioner, such as a surgeon, is conveniently provided with a kit of hooks 10 having a variety of diameters 56 such that the practitioner can select the apparatus 10 that has the diameter 56 to best fit the bone 8 of a subject during a surgical procedure.

Figure 6:
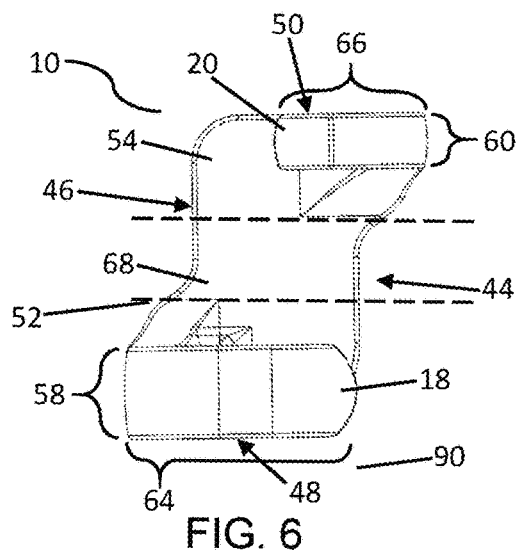
FIG. 6. A front view of the bone hook apparatus shown in FIG. 1.
Figure 7:
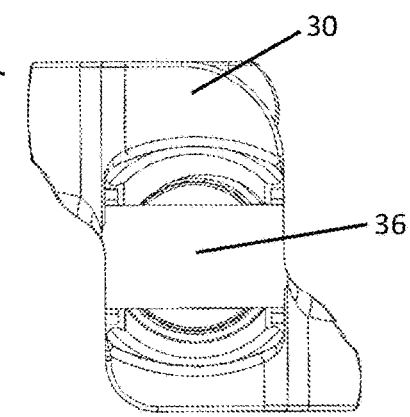
FIG. 7. A rear view of the bone hook apparatus shown in FIG. 1.

The first hook 18 may have a first hook length 64 that is longer than a second hook length 66 of the second hook 20. For example, the first hook 18 may extend to a front face plane 90 (FIG. 6) of the base 16, while the second hook 20 may extend to a mid-plane 92 (FIG. 4) of the base 16. Advantageously, in this configuration, the first hook 18 and the second hook 20 laterally overlap such that, when in use, they are configured to capture the bone 8 circumferentially for greater stability of the bone hook apparatus 10, while the shorter second hook 20 allows easier insertion of the bone 8 within the bone hook apparatus 10.

Figure 2:
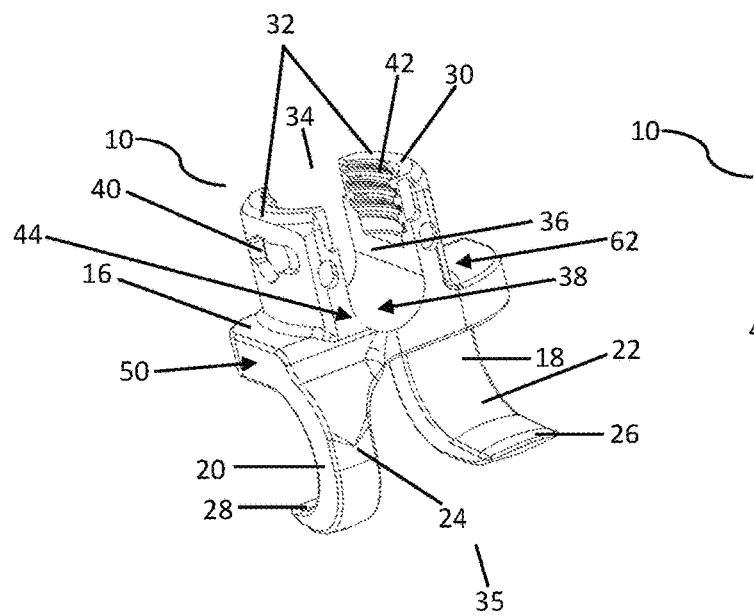
FIG. 2. A perspective view of the bone hook apparatus shown in FIG. 1.
Figure 3:
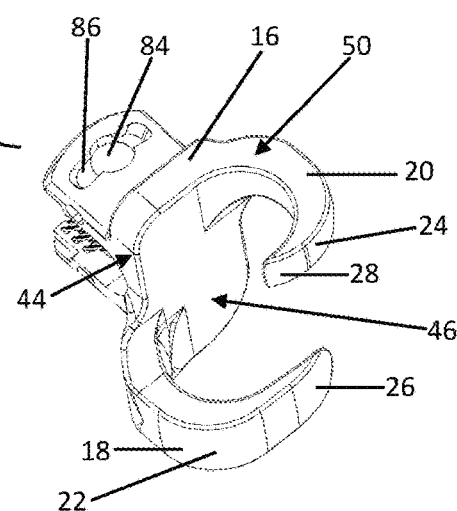
FIG. 3. An alternative perspective view of the bone hook apparatus shown in FIG. 1.

In the illustrated embodiment of the bone hook apparatus 10, the front face 44, the rear face 46, the first outer side face 48, and the second outer side face 50 variously define the first passage 52 and a second passage 54. The front face 44 is orthogonal to the rod channel 36 (as shown in FIGS. 2 and 3). The rear face 46 is orthogonal to the rod channel 36 and opposite the front face 44. An upper face 62 is disposed on the proximal side of the base 16. The rod channel 36 may extend in a direction between the front face 44 and the rear face 46. The first outer side face 48 extends from the front face 44 to the rear face 46, and includes the corresponding side of the base 16 and the outer side of the first hook 18. The second outer side face 50 extends from the front face 44 to the rear face 46, and includes the corresponding side of the base 16 and the outer side of the second hook 20. The first passage 52 is defined as running from front face 48 to the rear face 46, and bounded on either side by the first hook 18 and the second hook 20. The second passage 54 is perpendicular to the first passage 52, and extends the length of the base 16 so as to pass through the first hook 18 and the second hook 20. The second passage 54 is shown as orthogonal to the rod channel 36 in the accompanying drawings. The second passage 54 is configured to secure the bone hook apparatus 10 to the bone 8 when the first passage 52 is positioned over the bone 8 and rotated 90 degrees (as shown in FIGS. 10A-10C). In alternate embodiments, the rod channel 36 may be configured to run orthogonal to the first passage 52 and parallel to the second passage 54 (that is, the rod channel 36 may oriented from first outer side face 48 to the second outer side face 50) to accommodate attachment to an elongate bone structure to extending generally parallel to a desired orientation of the rod 12. The rod channel 36 may also be oriented such that it is transverse to both the first passage 52 and second passage 54 to accommodate attachment to an elongate bone structure that extends transverse to a desired rod orientation.

Figure 8A:
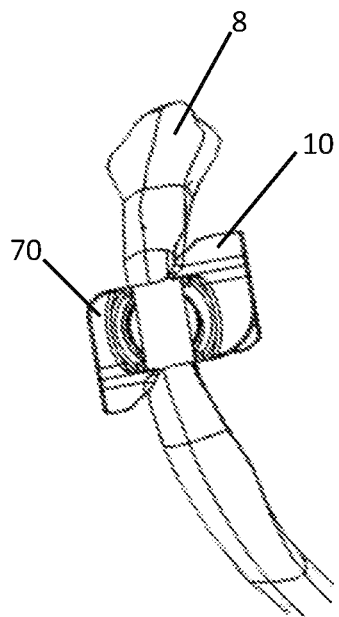
FIG. 8A. A top view of the bone hook apparatus shown in FIG. 1 positioned above a rib bone.
Figure 8B:
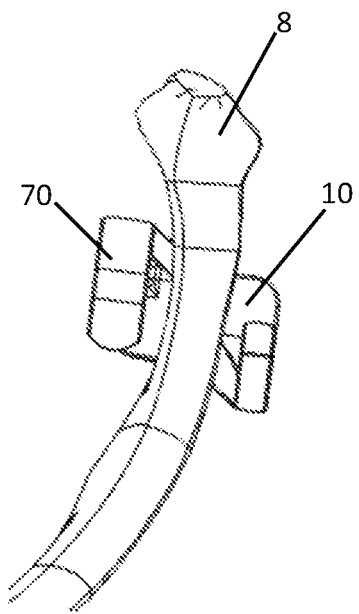
FIG. 8B. A rear view of the bone hook apparatus shown in FIG. 1 positioned above a rib bone.
Figure 9A:
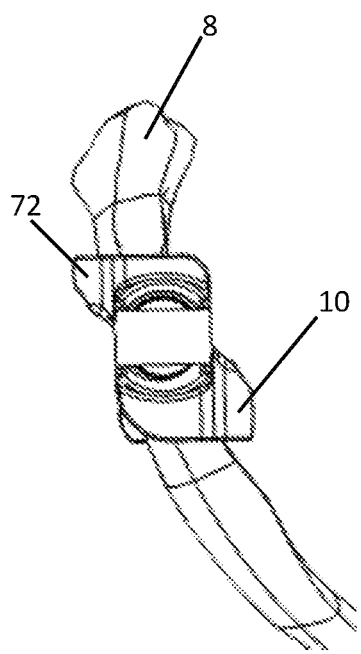
FIG. 9A. A top view of the bone hook apparatus shown in FIG. 8A after rotating the bone hook apparatus 90 degrees.
Figure 9B:
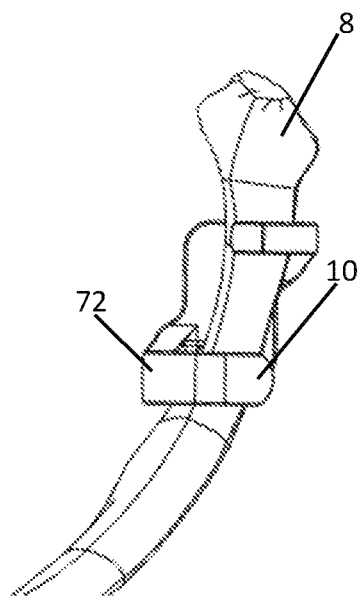
FIG. 9B. A rear view of the bone hook apparatus shown in FIG. 8b after rotating the bone hook apparatus 90 degrees.

In another aspect, a method of securing the bone hook apparatus 10 to the bone 8 is provided. The bone hook apparatus 10 may be positioned proximate to the bone 8, such as a rib, and lowered over the bone 8 such that the bone 8 traverses through the first passage 52 so that the first hook 18 and the second hook 20 are straddling opposing sides of the bone 8 (FIGS. 8A, 8B, and 10B) to form an initial orientation 70 of the bone hook apparatus 10. The bone hook apparatus 10 may be rotated, such as by 90 degrees clockwise or counterclockwise, to the final orientation 72 so that the first hook 18 and the second hook 20 are each at least partially under the bone 8 to align and capture the bone 8 within the second passage 54 (shown in FIGS. 9A, 9B, and 10C). The capturing of the bone 8 may trap, or securely fix, the bone 8 between the first hook 20 and the second hook 20. In the final orientation 72, the first hook 18 and the second hook 20 together circumferentially surround the bone 8. Advantageously, the final orientation 72 provides additional stability and support to load the bone hook apparatus 10 in all directions (e.g., cranial and caudal).

Figure 10D:
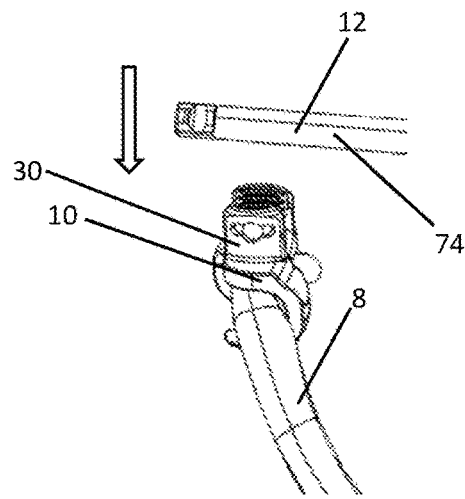
FIG. 10D. A perspective view of the bone hook apparatus shown in FIG. 10C with an associated rod.
Figure 10E:
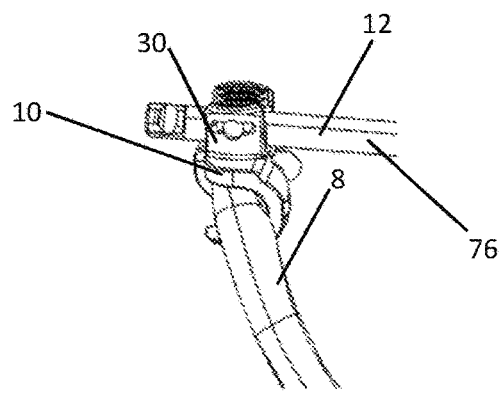
FIG. 10E. A perspective view of the bone hook apparatus shown in FIG. 10D with the associated rod disposed within a rod receptacle of the bone hook apparatus.
Figure 10F:
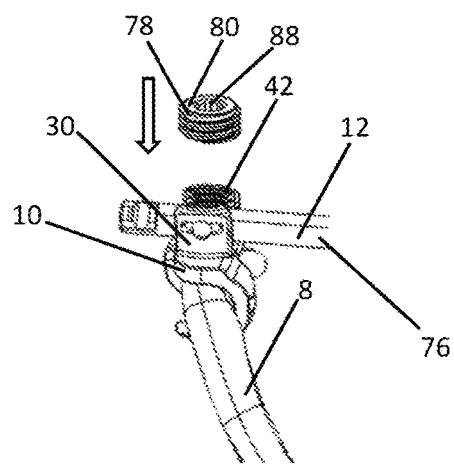
FIG. 10F. A perspective view of the bone hook apparatus shown in FIG. 10 with an associated locking cap.
Figure 10G:
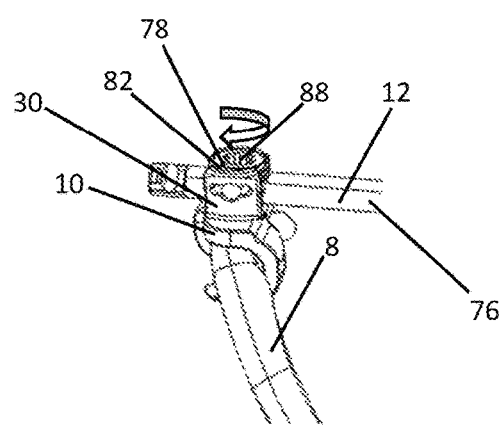
FIG. 10G. A perspective view of the bone hook apparatus shown in FIG. 10F with the associated locking cap engaged within the rod receptacle.

As shown in FIG. 10D, the rod 12 optionally may be positioned above the rod receptacle 30 in a first rod position 74. The rod 12 is inserted into the rod receptacle 30 after the bone hook apparatus 10 is in the final orientation 72 to form an implanted position 76 (FIG. 10E) of the rod 12. The rod 12 may then be secured by the locking cap engagement feature 42. For example, in the illustrated embodiment of the bone hook apparatus 10, the locking cap 78 is positioned in an unsecured locking cap position 80 above the rod 12 that is in the implanted position 76 (FIG. 10F). The locking cap 78 may then be lowered to engage the rod receptacle 30 into a secured locking cap position 82 (FIG. 10G) to securely fix the rod 12. Advantageously, the secured locking cap position 82 constrains the angular mobility of the bone hook apparatus 10 and prevents, or limits, translation of the rod 12 along its own longitudinal axis.

The bone hook apparatus 10 may be constructed of any suitable materials, including biocompatible materials. Some embodiments of the bone hook apparatus 10 are constructed of non-absorbable biocompatible materials. Specific examples of such suitable materials include. titanium, alloys of titanium, steel, stainless steel, and surgical steel. The bone hook apparatus 10, or parts thereof, could conceivably be made from non-metallic biocompatible materials, which include aluminum oxide, calcium oxide, calcium phosphate, hydroxyapatite, zirconium oxide, and polymers such as polypropylene. The bone hook apparatus 10 may be integrally formed.

It is to be understood that any given elements of the disclosed embodiments of the invention may be embodied in a single structure, a single step, a single substance, or the like. Similarly, a given element of the disclosed embodiment may be embodied in multiple structures, steps, substances, or the like.

The foregoing description illustrates and describes the processes, machines, manufactures, compositions of matter, and other teachings of the present disclosure. Additionally, the disclosure shows and describes only certain embodiments of the processes, machines, manufactures, compositions of matter, and other teachings disclosed, but, as mentioned above, it is to be understood that the teachings of the present disclosure are capable of use in various other combinations, modifications, and environments and are capable of changes or modifications within the scope of the teachings as expressed herein, commensurate with the skill and/or knowledge of a person having ordinary skill in the relevant art. The embodiments described hereinabove are further intended to explain certain best modes known of practicing the processes, machines, manufactures, compositions of matter, and other teachings of the present disclosure and to enable others skilled in the art to utilize the teachings of the present disclosure in such, or other, embodiments and with the various modifications required by the particular applications or uses. Accordingly, the processes, machines, manufactures, compositions of matter, and other teachings of the present disclosure are not intended to limit the exact embodiments and examples disclosed herein. Any section headings herein are provided only for consistency with the suggestions of 37 C.F.R. .sctn. 1.77 or otherwise to provide organizational queues. These headings shall not limit or characterize the invention(s) set forth herein.

The invention claimed is:

1. A bone hook apparatus for securing a rod to a bone, the bone hook apparatus comprising:
   a base;
   a rod receptacle disposed on a proximal side of the base;
   a first hook immovably associated with the base and extending therefrom, the first hook oriented in a first direction; and
   a second hook immovably associated with the base and extending distally therefrom, the second hook oriented in a second direction opposing the first direction, wherein the second hook is offset from the first hook, and the first hook and second hook together form a passage dimensioned to receive a portion of the bone therein,
   wherein in a first configuration of the bone hook apparatus, the passage is perpendicular to a direction in which the portion of the bone extends, and in a second configuration, the bone hook apparatus is rotated such that the passage is parallel to the direction in which the portion of the bone extends.

2. The bone hook apparatus of claim 1, wherein the rod receptacle comprises a first upright arm and a second upright arm opposite the first upright arm, and wherein the first hook and the second hook are joined to the first and second upright arms of the rod receptacle, respectively.

3. The bone hook apparatus of claim 1, wherein the base includes a first outer side face extending from the proximal face to the distal face, and wherein the first hook originates at or proximate to a junction of the proximal face and the first outer side face of the base.

4. The bone hook apparatus of claim 3, wherein the first outer side face includes a portion of an outer side of the first hook.

5. The bone hook apparatus of claim 3, wherein the base includes a second outer side face opposite the first outer side face and extending from the proximal face to the distal face, and wherein the second hook originates at or proximate to a junction of the proximal face and the second outer side face of the base.

6. The bone hook apparatus of claim 5, wherein the second outer side face extends from the proximal face to the distal face, and includes a portion of an outer side of the second hook.

7. The bone hook apparatus of claim 1, wherein the first hook has a first length that is longer than a second length of the second hook.

8. The bone hook apparatus of claim 7, wherein the first length extends across a length of the first outer side face of the base, and the second length extends to a mid-plane of the second outer side face of the base.

9. The bone hook apparatus of claim 1, wherein the first hook has a first height that is greater than a second height of the second hook.

10. The bone hook apparatus of claim 9, wherein an inner surface of the first hook and an inner surface of the second hook each has an arc shape, and the first height and the second height are each defined by a diameter of the arc shape of the first and second hooks, respectively.

11. The bone hook apparatus of claim 1, wherein the first hook has a first arm thickness that is greater than a second arm thickness of the second hook.

12. The bone hook apparatus of claim 11, wherein the first arm thickness is from 50% to 100% greater than the second arm thickness.

13. The bone hook apparatus of claim 1, wherein the first hook comprises a first arm and a first blade extending from and tapering away from the first arm in the first direction, and the first blade has a thickness that is smaller than a thickness of the first arm.

14. The bone hook apparatus of claim 1, wherein the first passage is configured to be positioned over the portion of the bone during insertion of the bond hook apparatus.

15. The bone hook apparatus of claim 1, further comprises a second passage perpendicular to the first passage, the second passage extending along a length of the base so as to pass through the first hook and the second hook.

16. The bone hook apparatus of claim 1, wherein one or more of the base, the rod receptacle, the first hook, and the second hook is formed from a biocompatible material.

17. The bone hook apparatus of claim 16, wherein the biocompatible material is selected from the group consisting of: titanium, a titanium alloy, steel, a steel alloy, stainless steel, surgical steel, and a combination thereof.

18. The bone hook apparatus of claim 1, wherein the first and second hooks are adapted to secure the rod to the bone selected from the group consisting of: a pediatric rib, an adult rib, a pediatric transverse process, an adult transverse process, a pediatric vertebral lamina, an adult vertebral lamina, and a combination thereof.

19. A kit comprising:
one or more bone hook apparatus for securing a rod to a bone, the bone hook apparatus comprising:
a base,
a rod receptacle disposed on a proximal face of the base,
a first hook integrally associated with the base and extending therefrom, the first hook oriented in a first direction, and
a second hook integrally associated with the base and extending distally therefrom, the second hook oriented in a second direction opposing the first direction, wherein the second hook is offset from the first hook, and the first hook and second hook together form a passage dimensioned to receive a portion of the bone therein,
wherein in a first configuration, the passage is perpendicular to a direction in which the portion of the bone extends, and in a second configuration, the bone hook apparatus is rotated such that the passage is parallel to the direction in which the portion of the bone extends;
the rod; and
a locking cap configured to secure the rod to the rod receptacle.

20. The kit of claim 19, comprising at least two hooks with diameters independently selected from a range between 4 mm and 16 mm.

* * * * *